(12) United States Patent
Sweeney

(10) Patent No.: US 7,819,922 B2
(45) Date of Patent: Oct. 26, 2010

(54) VERTEBRAL PROSTHESIS

(75) Inventor: Patrick J. Sweeney, Flossmoor, IL (US)

(73) Assignee: Spinal Generations, LLC, Olympia Fields, IL (US)

( * ) Notice: Subject to any disclaimer, the term of this patent is extended or adjusted under 35 U.S.C. 154(b) by 210 days.

(21) Appl. No.: 10/686,998

(22) Filed: Oct. 16, 2003

(65) Prior Publication Data

US 2005/0085910 A1 Apr. 21, 2005

(51) Int. Cl.
*A61F 2/44* (2006.01)
(52) U.S. Cl. ............... 623/17.16; 623/17.15; 623/23.47
(58) Field of Classification Search ... 623/17.11–17.16, 623/23.47
See application file for complete search history.

(56) References Cited

U.S. PATENT DOCUMENTS

| | | | |
|---|---|---|---|
| 4,496,090 A | 1/1985 | Crevier et al. | |
| 4,636,217 A | 1/1987 | Ogilvie et al. | |
| 4,759,769 A * | 7/1988 | Hedman et al. | 623/17.13 |
| 4,863,477 A | 9/1989 | Monson | |
| 4,932,975 A | 6/1990 | Main et al. | |
| 5,123,926 A | 6/1992 | Pisharodi | |
| 5,147,404 A | 9/1992 | Downey | |
| 5,171,278 A | 12/1992 | Pisharodi | |
| 5,246,458 A | 9/1993 | Graham | |
| 5,306,310 A | 4/1994 | Siebels | |
| 5,458,638 A | 10/1995 | Kuslich et al. | |
| 5,474,551 A | 12/1995 | Finn et al. | |
| 5,480,442 A * | 1/1996 | Bertagnoli | 623/17.14 |
| 5,533,084 A | 7/1996 | Mazess | |
| 5,571,190 A | 11/1996 | Ulrich et al. | |
| 5,665,122 A | 9/1997 | Kambin | |
| 5,702,453 A | 12/1997 | Rabbe et al. | |
| 5,776,197 A | 7/1998 | Rabbe et al. | |
| 5,776,198 A | 7/1998 | Rabbe et al. | |
| 5,776,199 A | 7/1998 | Michelson | |
| 5,782,830 A | 7/1998 | Farris | |
| 5,827,328 A * | 10/1998 | Buttermann | 623/17.13 |
| 5,895,427 A | 4/1999 | Kuslich et al. | |
| 5,895,428 A | 4/1999 | Berry | |
| 6,015,436 A | 1/2000 | Schonhoffer | |
| 6,038,281 A | 3/2000 | Mazess | |
| 6,066,174 A | 5/2000 | Farris | |
| 6,086,613 A | 7/2000 | Camino et al. | |
| 6,106,557 A | 8/2000 | Robioneck et al. | |
| 6,149,686 A | 11/2000 | Kuslich et al. | |
| 6,159,211 A | 12/2000 | Boriani et al. | |
| 6,176,881 B1 | 1/2001 | Schar et al. | |
| 6,296,665 B1 | 10/2001 | Strnad et al. | |
| 6,344,057 B1 | 2/2002 | Rabbe et al. | |

(Continued)

OTHER PUBLICATIONS

International Search Report and Written Opinion for Application No. PCT/US04/33765, date of mailing Jun. 29, 2005, 10 pages.

*Primary Examiner*—Corrine McDermott
*Assistant Examiner*—Cheryl Miller
(74) *Attorney, Agent, or Firm*—Foley & Lardner LLP

(57) ABSTRACT

A vertebral prosthesis is adapted to be implanted adjacent a spinal disc prosthesis. According to one embodiment, the vertebral prosthesis includes a shaft and an endplate coupled to one end of the shaft. The endplate is adapted to be implanted adjacent a disc prosthesis, thereby obviating the need to fuse the endplate to an adjacent vertebral body.

22 Claims, 14 Drawing Sheets

U.S. PATENT DOCUMENTS

| | | |
|---|---|---|
| 6,375,681 B1 | 4/2002 | Truscott |
| 6,375,682 B1 * | 4/2002 | Fleischmann et al. ..... 623/17.12 |
| 6,395,030 B1 | 5/2002 | Songer et al. |
| 6,413,278 B1 | 7/2002 | Marchosky |
| 6,443,987 B1 | 9/2002 | Bryan |
| 6,488,710 B2 | 12/2002 | Besselink |
| 6,500,206 B1 | 12/2002 | Bryan |
| 6,520,993 B2 | 2/2003 | James et al. |
| 6,524,341 B2 | 2/2003 | Lang et al. |
| 6,613,051 B1 | 9/2003 | Luk et al. |
| 7,235,102 B2 * | 6/2007 | Ferree et al. ............. 623/17.12 |
| 7,563,281 B2 * | 7/2009 | Sears et al. .............. 623/17.11 |
| 7,628,815 B2 * | 12/2009 | Baumgartner et al. .... 623/17.15 |
| 7,641,693 B2 * | 1/2010 | Gutlin et al. ............. 623/17.15 |
| 2001/0032020 A1 | 10/2001 | Besselink |
| 2002/0107572 A1 | 8/2002 | Foley et al. |
| 2002/0115944 A1 | 8/2002 | Mendes et al. |
| 2002/0161441 A1 | 10/2002 | Lang et al. |
| 2002/0169508 A1 | 11/2002 | Songer et al. |
| 2004/0172129 A1 | 9/2004 | Schafer et al. |
| 2005/0060034 A1 * | 3/2005 | Berry et al. .............. 623/17.11 |
| 2005/0071007 A1 | 3/2005 | Malek |
| 2005/0113924 A1 * | 5/2005 | Buttermann ............. 623/17.13 |
| 2005/0228501 A1 | 10/2005 | Miller et al. |
| 2006/0100710 A1 | 5/2006 | Gutlin et al. |

* cited by examiner

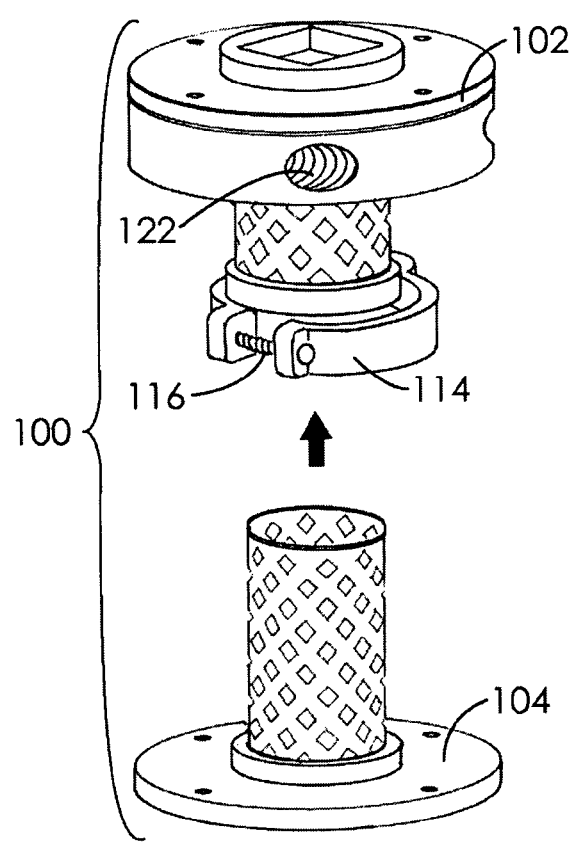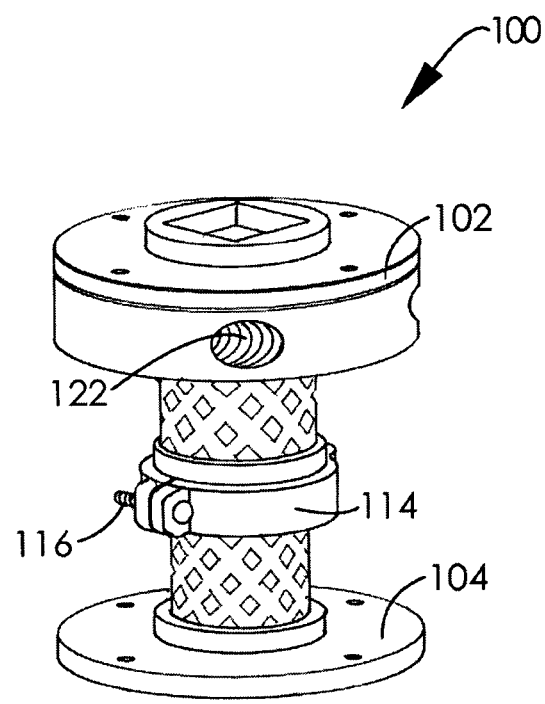
Fig. 17
Fig. 18

VERTEBRAL PROSTHESIS

FIELD OF THE INVENTION

The present invention relates to a vertebral prosthesis, used to replace a spinal vertebra. In particular, the present invention relates to a vertebral prosthesis that is used in conjunction with disc prostheses to avoid the need for a spinal fusion procedure.

BACKGROUND OF THE INVENTION

The spinal column is comprised of twenty-six interlocking vertebrae. These vertebrae are separated by discs. The spine provides load bearing support for one-half of the body's mass and it protects the nerves of the spinal column. The discs provide shock absorption and facilitate the bending of the spine.

The combination of the vertebrae and discs at each vertebral segment allows for motion of the spine, in particular, flexing, rotation, and extension. The motion and support functions of the spine, in combination with the many interlocking parts and nerve roots associated with the spinal column can result in back pain due to various reasons. Such back pain may result from the degeneration of discs due to age, disease, or injury. Further, vertebral bodies may be compromised due to disease or defect, such as a tumor, or injury, such as a fracture. In certain cases, it becomes necessary to remove or replace one or more of the vertebral bodies or discs to alleviate pain or regain spinal functionality.

Spinal fusion or lumbar spinal fusion is one way to treat a compromised vertebral body due to unstable burst fractures, severe compression fractures, and tumor decompression. In a spinal fusion procedure, the discs above and below the compromised vertebral body are removed and a strut graft and plate are then used to make the vertebrae above and below the replaced vertebral body grow together and become one bone. More surgery may be necessitated in the future as the adjacent spine wears out. The function of a fused spine is usually diminished compared to a normal spine because the flexibility of the fused segments is removed. Because the intention of a spinal fusion procedure is to create solid bone in the area that is excised, the spacer that is inserted to restore normal height may be configured to enhance bone in-growth, which may be enhanced by the addition of bone growth material.

Pedicle screws are becoming more common in spine surgery because of their use in stabilizing the spine. The pedicle is a strong point of attachment in the spine, so pedicle screws may be attached between a vertebral prosthesis and the adjacent pedicle to fix the prosthesis in place. Screws are inserted through the cancellous bone of the pedicle into the vertebral prosthesis.

There is a need for a vertebral prosthesis that is configured to be used in conjunction with artificial disc replacements above and below the replaced vertebra, thus preserving the motion and stability of the vertebral segment by obviating the need for a spinal fusion procedure. Further, there is a need for a vertebral prosthesis that may be used with or without a spinal fusion procedure to provide flexibility to the surgeon performing the vertebral replacement surgery. Further still, there is a need for a vertebral prosthesis that is configured to be used in conjunction with artificial discs having different configurations in order to provide procedural flexibility. Further still, there is a need for a vertebral prosthesis that is configured to be used with or without pedicle screws.

It would be desirable to provide a system and/or procedure that provides one or more of these or other advantageous features. Other features and advantages will be made apparent from the present specification. The teachings disclosed extend to those embodiments that fall within the scope of the appended claims, regardless of whether they accomplish one or more of the aforementioned needs.

SUMMARY OF THE INVENTION

The invention relates to a spinal implant system. The spinal implant system includes vertebral prosthesis having a support and an endplate. The spinal implant system further includes an artificial spinal disc coupled to the endplate.

The invention further relates to a vertebral prosthesis adapted to replace a vertebra. The vertebral prosthesis includes a shaft and an endplate coupled to one end of the shaft, the endplate adapted to be implanted adjacent a disc prosthesis, obviating the need to fuse the endplate to an adjacent vertebrae.

Further still, the invention relates to a vertebral prosthesis that is compatible with multiple disc prostheses. The vertebral prosthesis includes a shaft and an endplate tray coupled to the shaft. The endplate tray is configured to be implanted adjacent a first artificial disc having a first shape, or, alternatively, a second artificial disc having a second shape.

Further still, the invention relates to a method of replacing a vertebral body and at least one adjacent spinal disc. The method includes the steps of opening an aperture in a patient to permit access to a vertebral body to be replaced, removing the vertebral body, and removing a spinal disc located adjacent the vertebral body. The method further includes the steps of selecting a vertebral prosthesis to be implanted into the space created by the removal of the vertebral body and the spinal disc and selecting an artificial disc to be implanted between the vertebral prosthesis and an adjacent vertebra. Further, the method includes the steps of coupling the vertebral prosthesis to the artificial disc, coupling the artificial disc to the adjacent vertebra, and closing the aperture.

The invention is capable of other embodiments and of being practiced or being carried out in various ways. Alternative exemplary embodiments relate to other features and combinations of features as may be generally recited in the claims.

BRIEF DESCRIPTION OF THE DRAWINGS

The invention will become more fully understood from the following detailed description, taken in conjunction with the accompanying drawings, wherein like reference numerals refer to like elements, in which:

FIG. 17 is a perspective view of the vertebral prosthesis of FIG. 15 prior to assembly;

FIG. 18 is a perspective view of the vertebral prosthesis of FIG. 17 after assembly;

DESCRIPTION OF PREFERRED EMBODIMENTS

Figure 1:
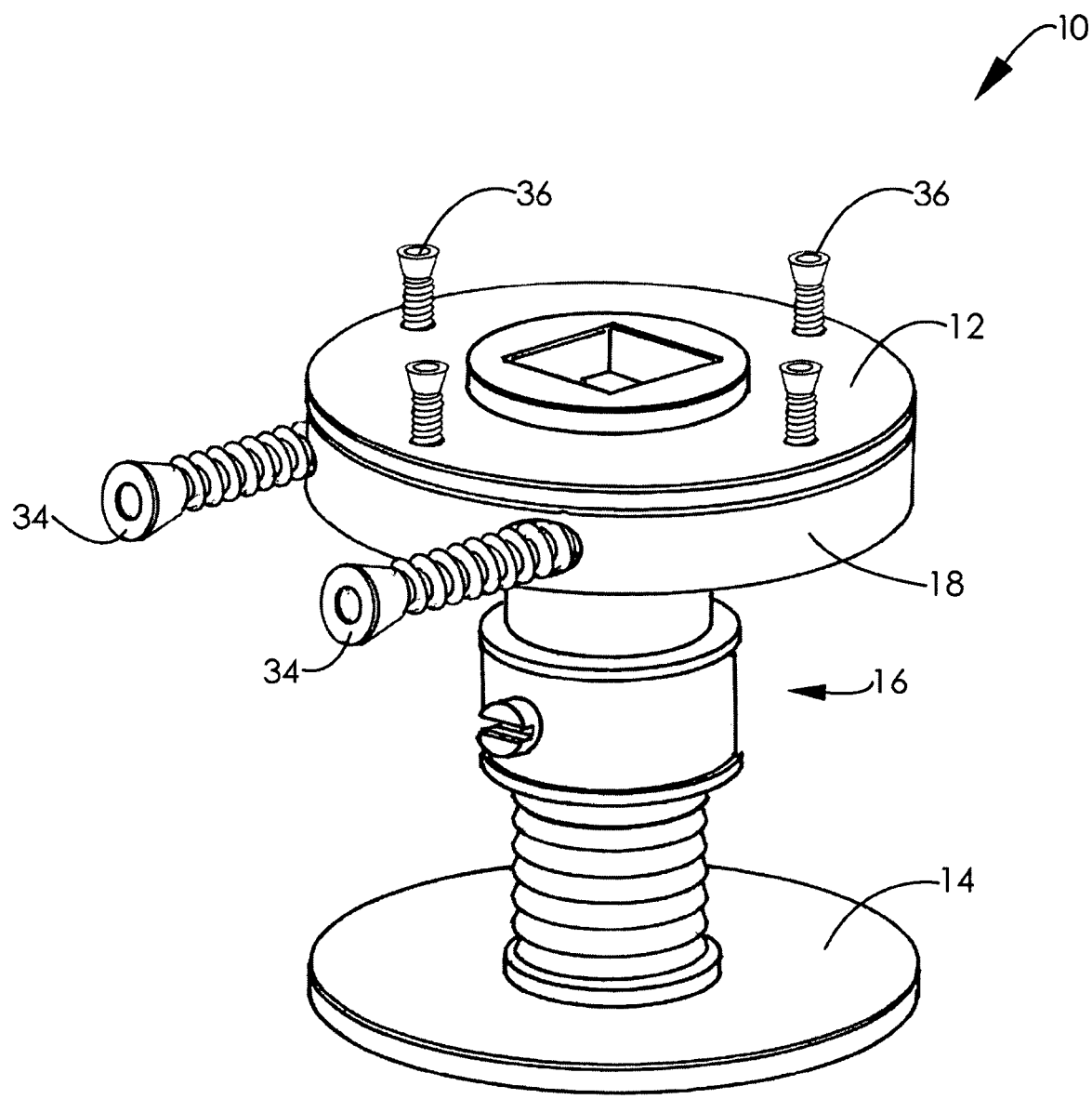
FIG. 1 is a perspective view of a vertebral prosthesis.

Referring to FIG. 1, according to an exemplary embodiment, a vertebral prosthesis or artificial vertebral body, shown as vertebral prosthesis 10, includes a pair of endplates, shown as endplate trays 12, 14. The endplate trays 12, 14 are connected to one another by a support, shown as shaft 16. A pedicle screw retainer or support 18 may be coupled to the shaft 16 and connected to one of the endplate trays 12, 14. In the depicted embodiment, pedicle screw support 18 is affixed to shaft 16 adjacent the upper endplate tray 12.

Referring to FIGS. 2-5, in an exemplary embodiment, the vertebral prosthesis 10 has a shaft upper portion 20 and a shaft lower portion 22. A locking ring 24 may be held in place by a washer 26 and used to connect lower portion 22 to upper portion 20. In the embodiment shown in FIGS. 2-5, shaft lower portion 22 is received within cylindrically shaped shaft upper portion 20 and fixed in place by a fixation device, shown as screw 28. The use of locking ring 24 and screw 28 permits the height of shaft 16 to be adjusted as desired by the surgeon.

Figure 2:
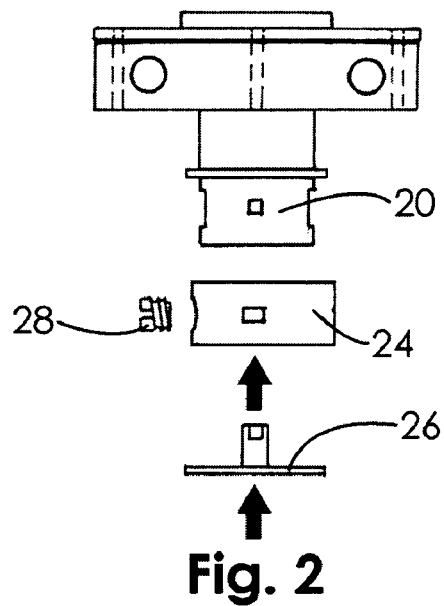
FIG. 2 is an elevation view of the components of the upper portion of a vertebral prosthesis prior to assembly.
Figure 3:
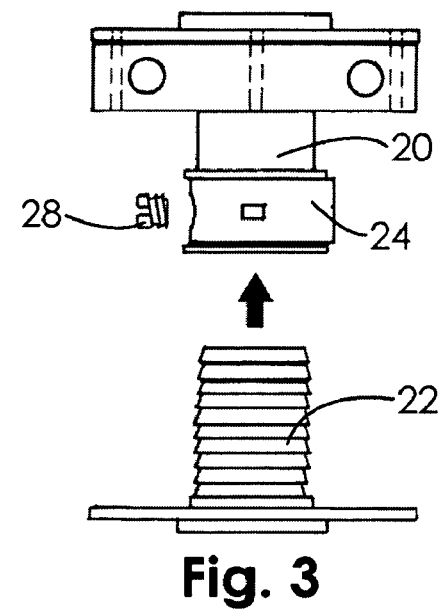
FIG. 3 is an elevation view of the components of a vertebral prosthesis prior to assembly.
Figure 4:
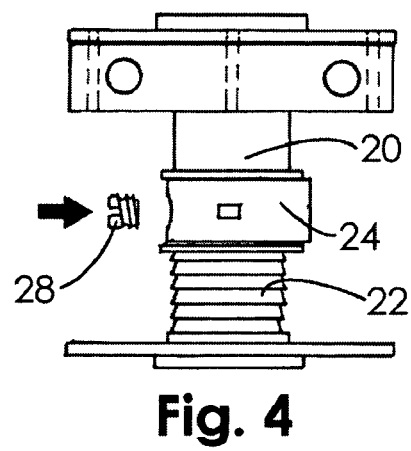
FIG. 4 is an elevation view of a vertebral prosthesis and locking screw prior to assembly.
Figure 5:
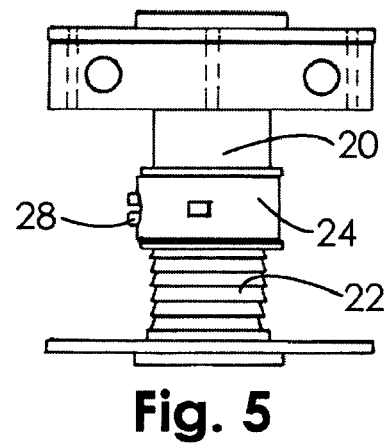
FIG. 5 is an elevation view of an assembled vertebral prosthesis.
Figure 6:
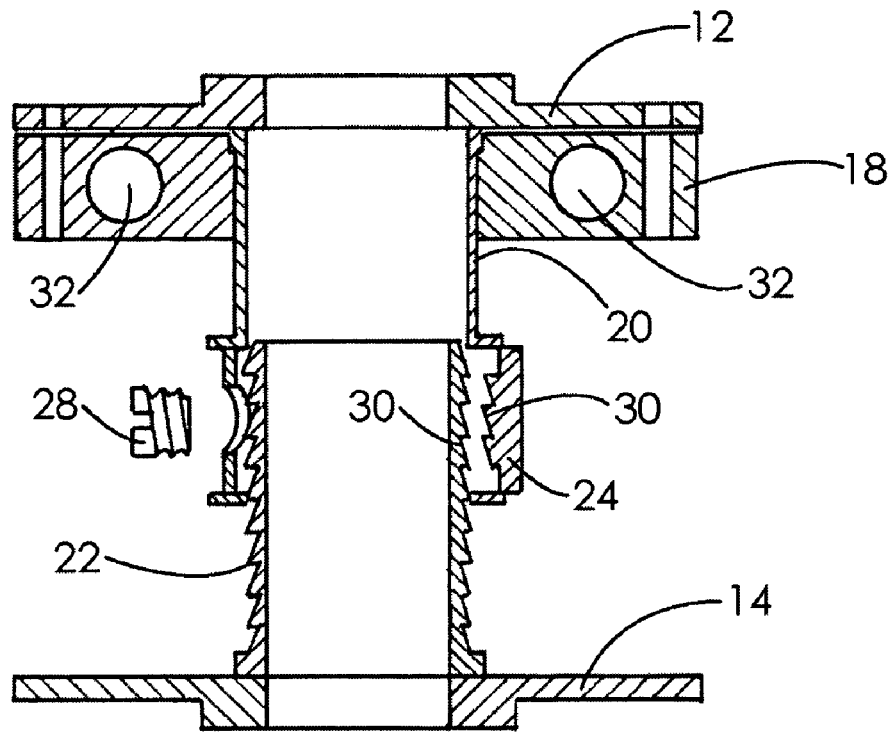
FIG. 6 is a sectional view of a vertebral prosthesis prior to insertion of a locking screw.
Figure 7:
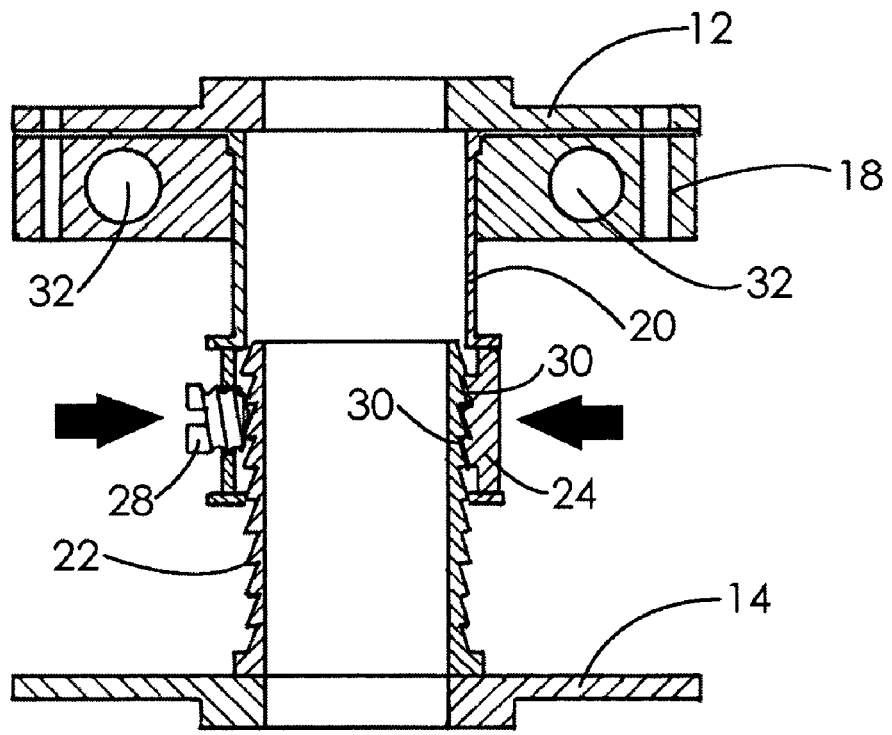
FIG. 7 is a sectional view of an assembled vertebral prosthesis.

Referring to FIGS. 6 and 7, in an exemplary embodiment, locking ring 24 locks shaft upper portion 20 and shaft lower portion 22 into position relative to each other via interlocking teeth 30 on both the locking ring 24 and shaft lower portion 22 that engage one another when screw 28 is tightened as indicated in FIG. 7. Locking ring 24 is fixed relative to shaft upper portion 20 as shown in FIGS. 2 and 3.

Further referring to FIGS. 6 and 7, pedicle screw support 18 may include pedicle screw apertures 32 that receive and interlock with pedicle screws 34 as shown in FIG. 1. The pedicle screw support 18 may be attached to the endplate tray 12 by screws or any other suitable attachment mechanism, such as tray screws 36 shown in FIG. 1.

Figure 8:
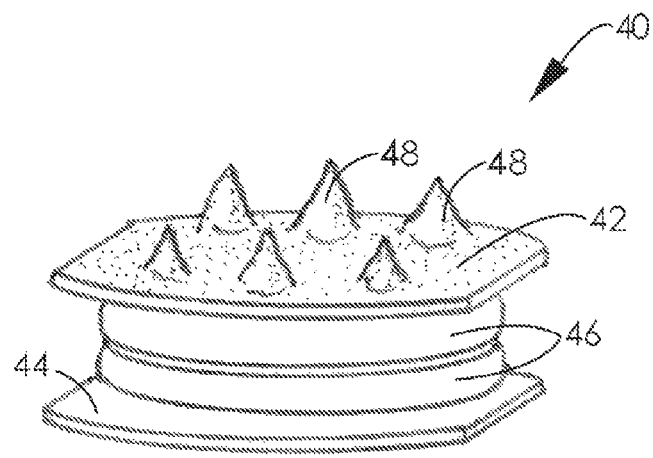
FIG. 8 is a perspective view of a disc prosthesis.

Referring to FIG. 8, an artificial spinal disc or spinal disc prosthesis, shown as artificial disc 40, may be used to replace a natural disc that is excised during vertebral body replacement surgery. When used in a spinal disc replacement surgery, artificial disc 40 typically includes plates, such as endplates 42, 44, adjacent a bearing surface or core 46. The endplates 42, 44 typically have teeth 48 that help endplates 42, 44 anchor into the adjacent vertebrae. The core 46 may be made of rubber and the endplates may be made of chrome.

Figure 9:
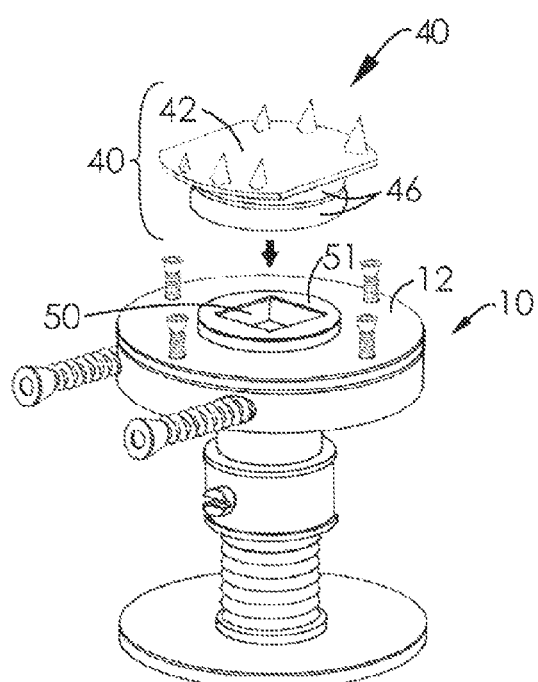
FIG. 9 is a perspective view of a disc prosthesis and a vertebral prosthesis prior to assembly with one another.

Referring to FIG. 9, when used in conjunction with vertebral prosthesis 10, artificial disc 40 may be used with one endplate removed such that core 46 directly couples with endplate tray 12. In one embodiment, endplate tray 12 is manufactured with a recess 50 that is configured to receive a specific artificial disc having a core of a particular configuration.

Figure 10:
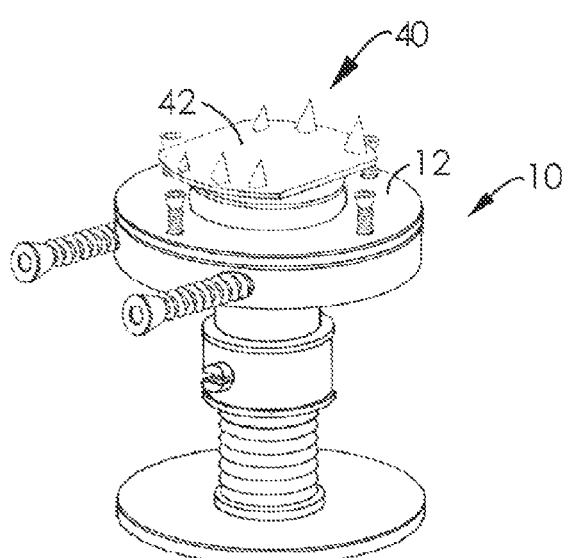
FIG. 10 is a perspective view of a disc prosthesis and a vertebral prosthesis after assembly with one another.

Referring to FIG. 10 in one embodiment, core 46 fits into and laterally interlocks with a structure shown as recess 50 and corresponding flange 51 in endplate tray 12. Recess 50 and flange 51 are built up above the corresponding endplate tray to mimic the proper relationship between the disc prosthesis and a vertebra. Additional attachment means between artificial disc 40 and vertebral prosthesis 10 are not needed once the combination is installed in the spine because the compression between adjacent vertebrae prevents artificial disc 40 from pulling out of and being displaced from recess 50. In an exemplary embodiment, recess 50 and flange 51 are configured similarly to the structure of endplate 44 (see FIG. 8) that is removed to permit artificial disc 40 to be used in conjunction with vertebral prosthesis 10. It is to be understood that recess 50 and flange 51 are but one embodiment of the many structures that may be used to interlock or couple with different artificial discs. Depending on the disc configuration, various recesses and/or flanges may be used to create the proper structure.

Figure 11:
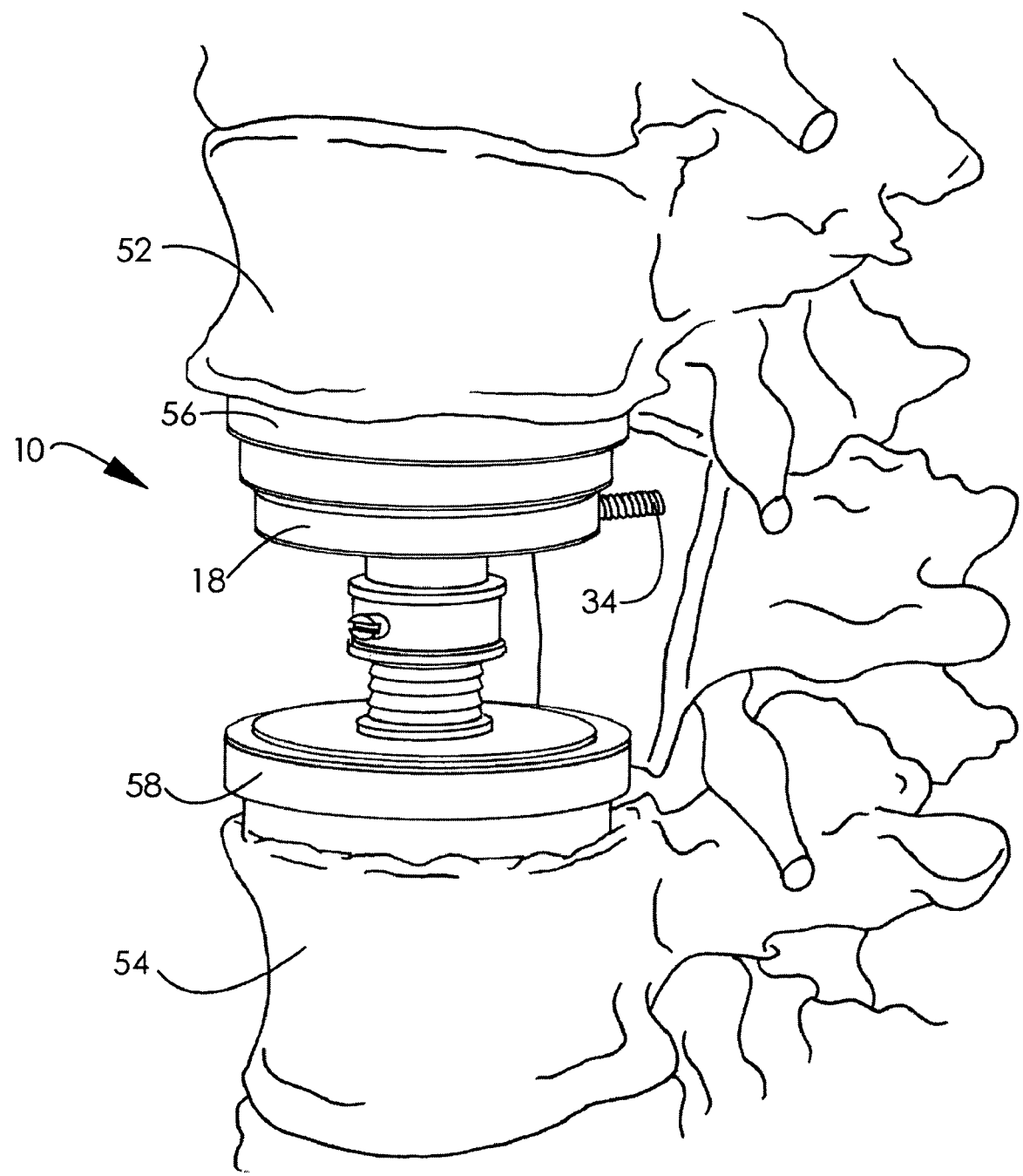
FIG. 11 is a perspective view of a vertebral prosthesis and two disc prostheses inserted into a spine.

FIG. 11 depicts vertebral prosthesis 10 installed in a spine in accordance with one exemplary embodiment. In the example shown, a diseased or injured vertebra has been removed and the vertebral prosthesis 10 has been inserted between a superior vertebra 52 and an inferior vertebra 54. Further, the two natural discs have been excised and replaced with superior and inferior prosthetic discs 56, 58. The depicted embodiment includes pedicle screw support 18 used with pedicle screw 34. The prosthesis discs 56, 58 may be of various types and configurations, and are not limited to the specific embodiments shown in FIG. 11 or the other Figures. Examples may include a PRODISC artificial disc manufactured by Synthes, a SB CHARITE III artificial disc made by Waldemar Link GmbH and Company, or the spinal disc prosthesis system described in copending application Ser. No. 10/619,757, which is incorporated by reference herein in its entirety.

Figure 12:
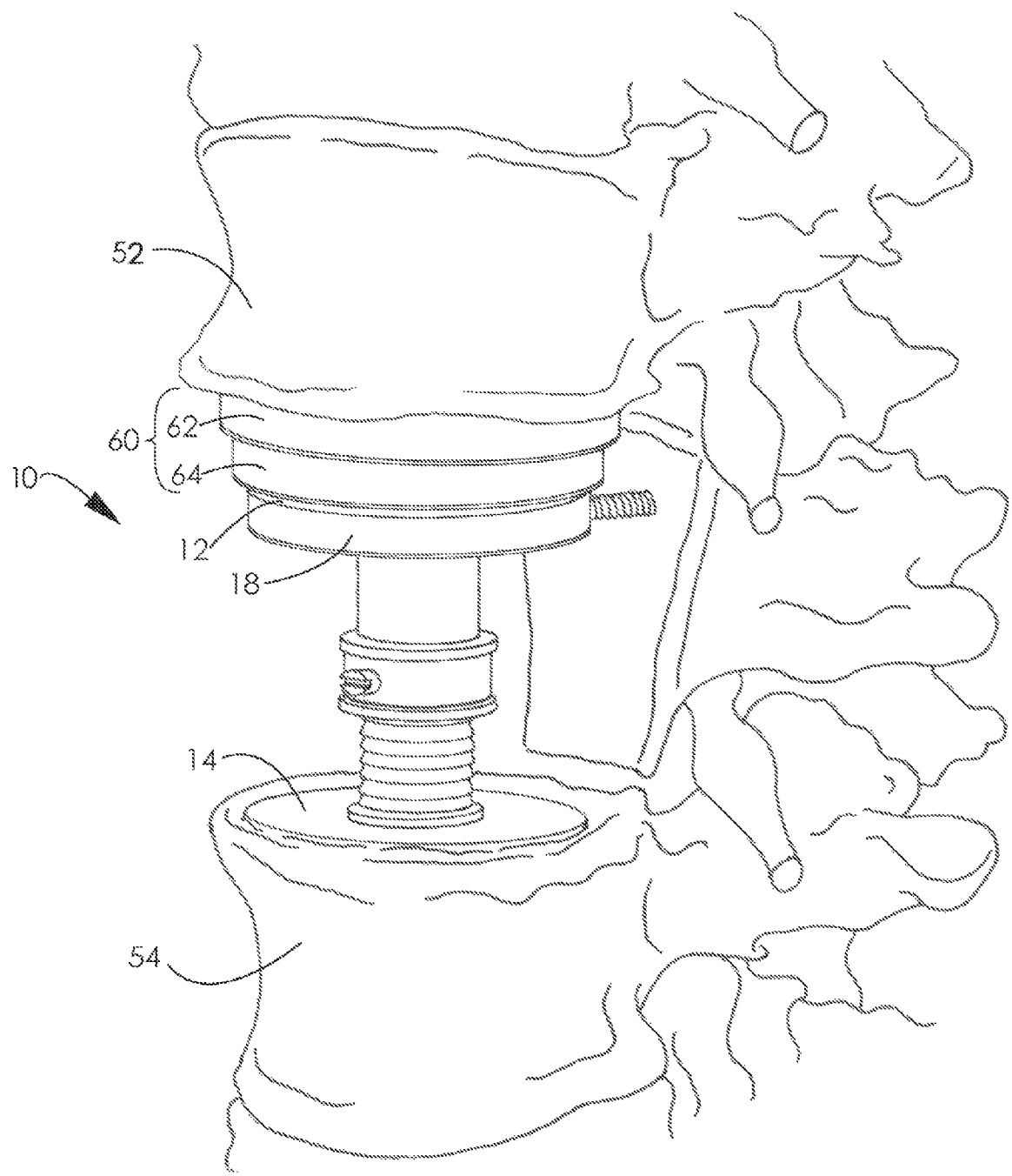
FIG. 12 is a perspective view of a vertebral prosthesis and one disc prosthesis inserted into a spine.

FIG. 12 depicts usage of the vertebral prosthesis 10 in conjunction with a spinal disc prosthesis 60, such as that described in copending U.S. application Ser. No. 10/619,757. Disc prosthesis 60 includes a pair of nested cups. In the view of FIG. 12, superior cup 62 and inferior cup 64 are shown. Inferior cup 64 attaches directly to endplate tray 12, which is specifically configured to couple to inferior cup 64. In one embodiment, the endplate tray is cast as a single component with inferior cup 64. Vertebral prosthesis 10 may be installed in conjunction with a single prosthetic disc 60 while the lower endplate tray 14 is directly attached to the inferior vertebra 54. This approach allows fusion of the inferior interspace while preserving motion at the superior interspace. In order to attach to the inferior vertebra 54, the lower endplate tray 14 may be configured with teeth or spikes (not shown) that interface directly with inferior vertebra 54. While the lower endplate 14 is shown as coupling directly to inferior vertebra 54 in the exemplary embodiment of FIG. 12, the vertebral prosthesis 10 may be configured such that the upper endplate tray 12 attaches directly to the superior vertebra 52 and the lower endplate 14 attaches to an artificial disc. The vertebral prosthesis system of the present invention is intended to be configured and reconfigured in many different ways to provide flexibility during the performance of vertebral body surgery.

Figure 13:
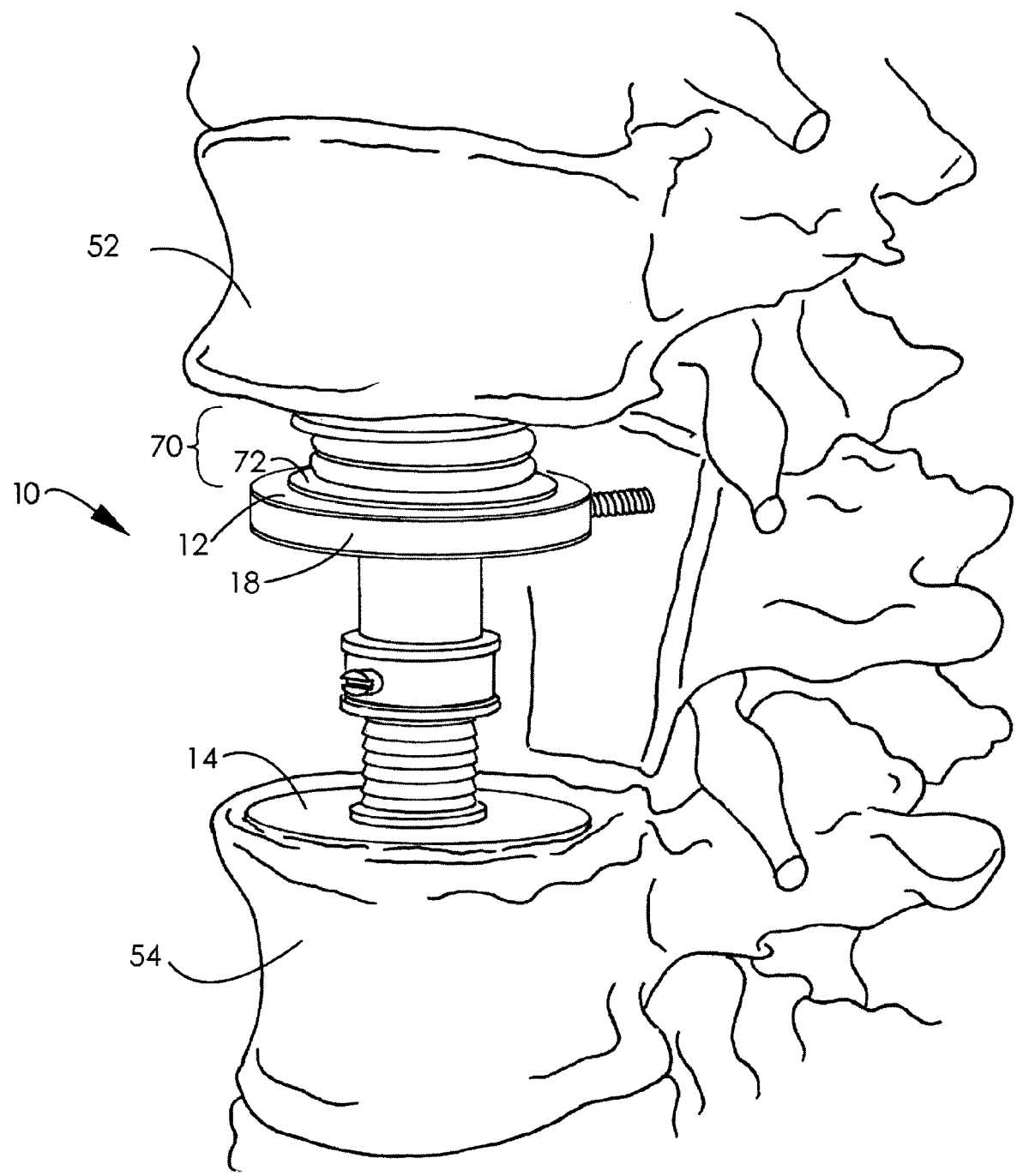
FIG. 13 is a perspective view of a vertebral prosthesis and one disc prosthesis inserted into a spine.

Referring to FIG. 13, vertebral prosthesis 10 is shown as installed with one endplate tray 14 installed directly into inferior vertebra 54, such as by engagement with spikes and the endplate tray 14. Disc prosthesis 70 is installed between upper endplate tray 12 and superior vertebra 52. In one embodiment, disc prosthesis 70 is a SB CHARITE III artificial disc and the upper endplate tray 12 includes a structure, shown as integral flange 72 that serves as a lower endplate for the disc prosthesis 70.

Figure 14:
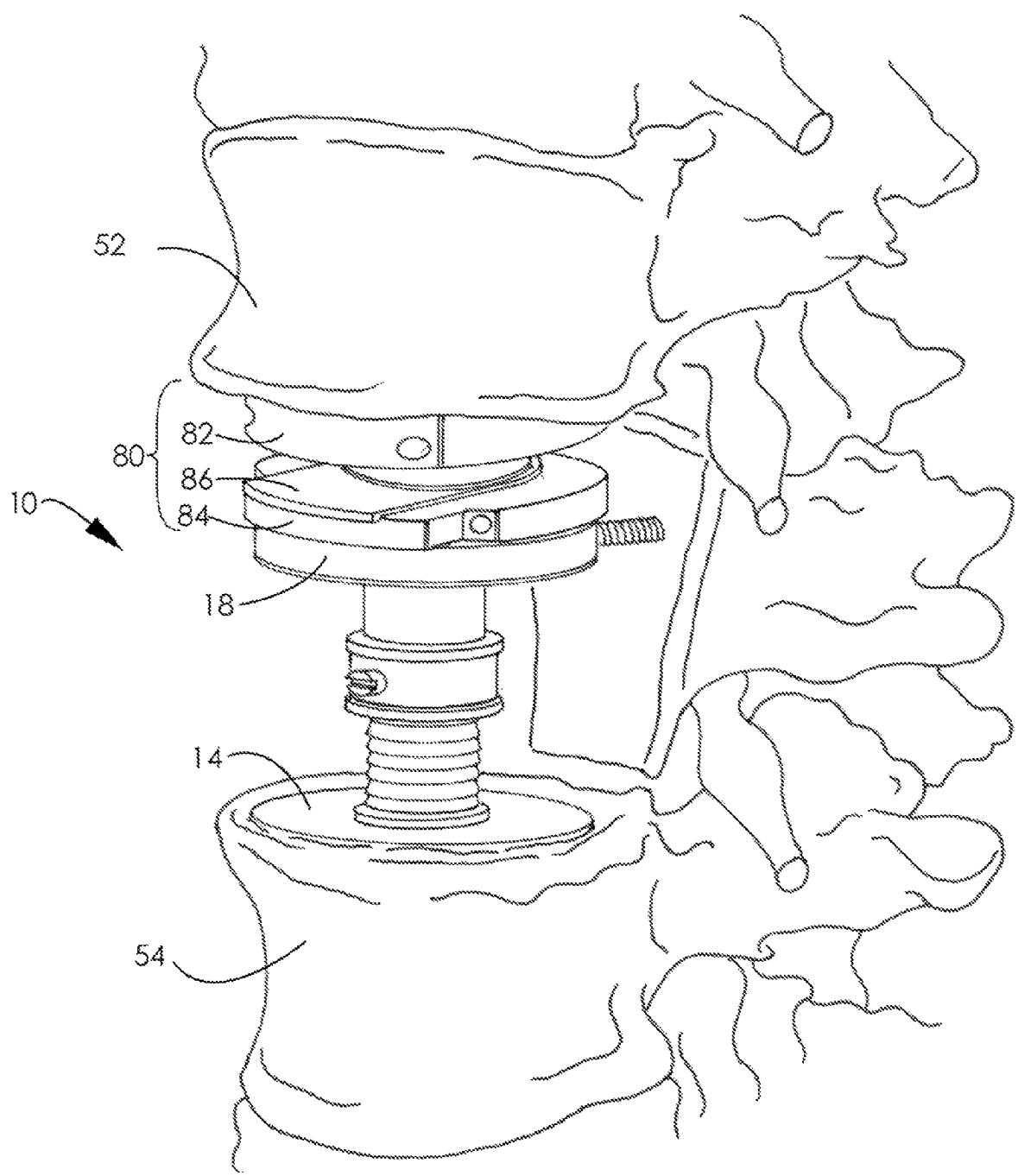
FIG. 14 is a perspective view of a vertebral prosthesis and one disc prosthesis inserted into a spine.

Referring to FIG. 14, vertebral prosthesis 10 is shown as installed in conjunction with disc prosthesis 80. Disc prosthesis 80 includes a superior endplate 82, an inferior endplate 84 and a core or bearing surface 86 situated between the superior and inferior endplates 82, 84. The inferior endplate 84 is cast as one piece with endplate tray 12. In other embodiments, inferior endplate may be connected in other ways with the endplate tray of the vertebral prosthesis. While disc prosthesis 80 is shown as attached between upper endplate tray 12 and superior vertebra 52, an additional disc prosthesis similar to disc prosthesis 80 or one of a completely different configuration may be placed between lower endplate tray 14 and inferior vertebra 54 depending on the needs of the patient. Disc prosthesis 80 may be a PRODISC device in an exemplary embodiment.

In the various embodiments described herein, the endplates of the vertebral prosthesis are shown as being used with various artificial discs. This flexibility may be achieved by utilizing different endplates having structures intended for use with specific discs. For example, a particular endplate may be cast to match the shape of a particular artificial disc. The endplates may be easily interchangeable for use on the same support or shaft. In other embodiments, a single endplate may have a structure intended to interlock with two or more different types or shapes of artificial discs.

Figure 15:
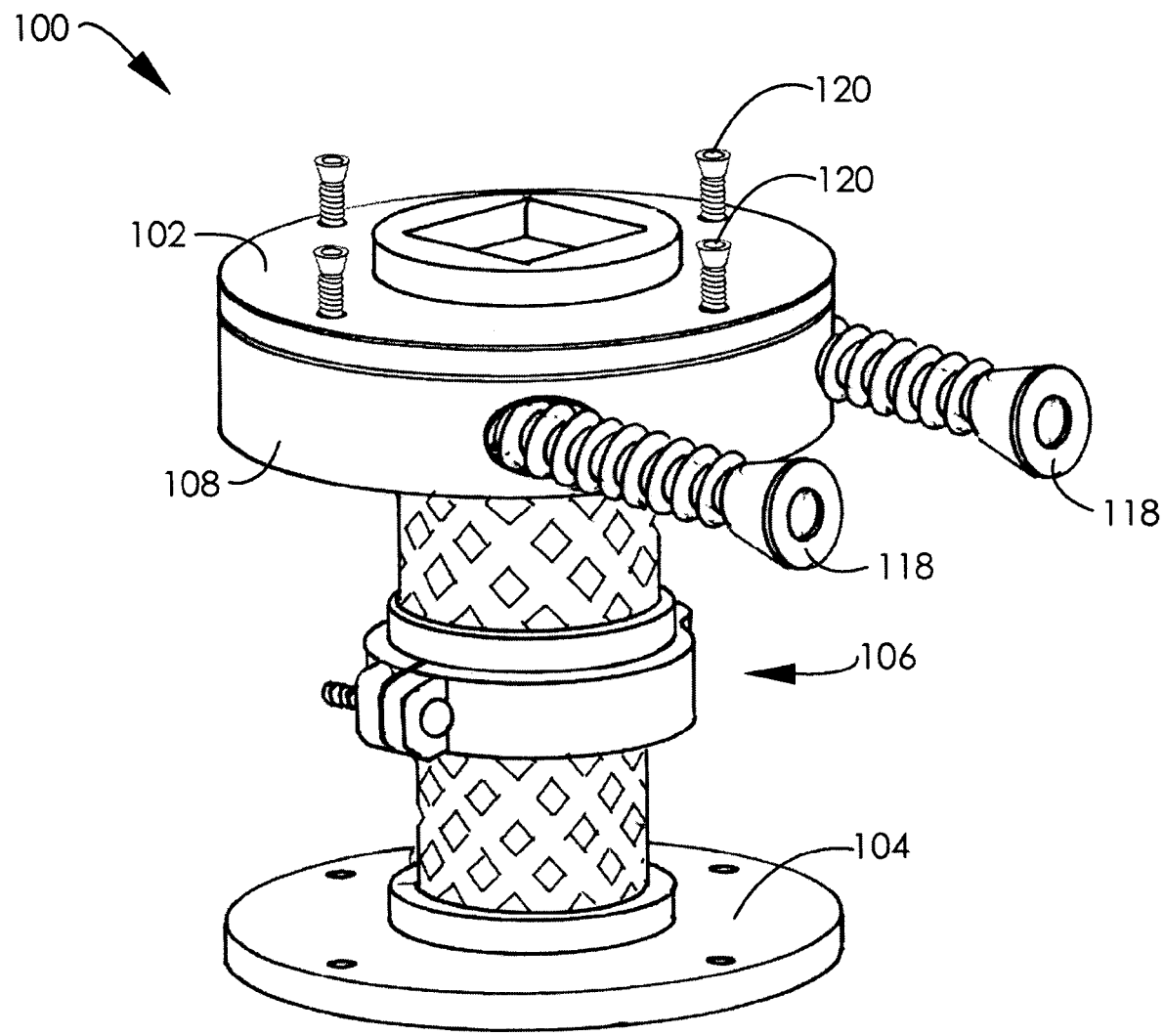
FIG. 15 is a perspective view of a vertebral prosthesis according to another exemplary embodiment.

Referring to FIG. 15, according to an additional exemplary embodiment, vertebral prosthesis 100 includes upper and lower endplate trays 102, 104 that are interconnected by a shaft 106. Shaft 106 is shown as being a mesh, which may be metallic or a composite. A pedicle screw support 108 is shown as being located adjacent to upper endplate tray 102 but may be adjacent the lower endplate tray 104 or omitted entirely. Pedicle screws 118 are received in the pedicle screw support 108.

Figure 16:
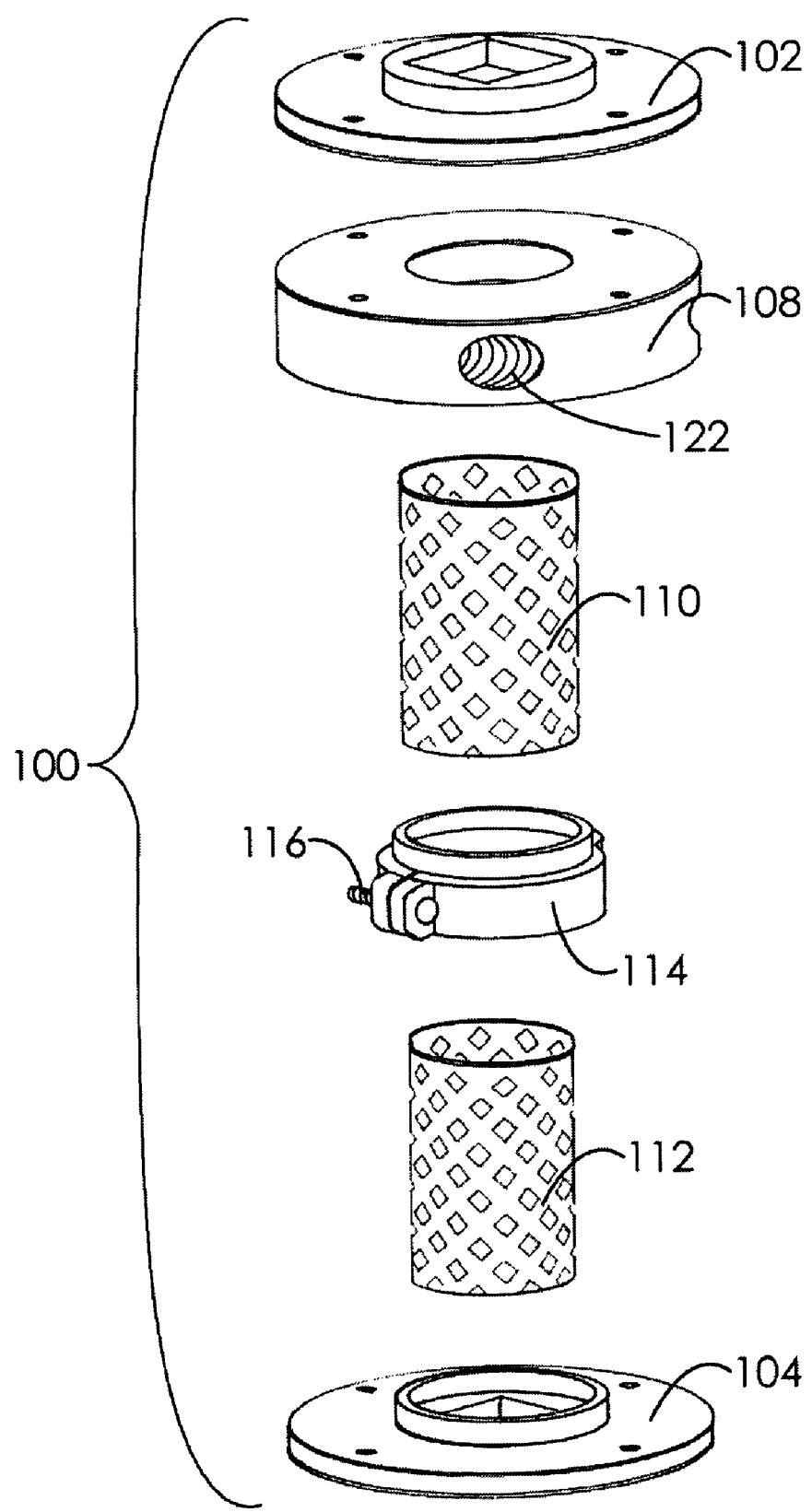
FIG. 16 is an exploded perspective view of the vertebral prosthesis of FIG. 15.

Referring to FIG. 16, in an exemplary embodiment of vertebral prosthesis 100, a shaft lower portion 112 is configured to be received within shaft upper portion 110 and locked into position relative to one another by ring 114 and a tightening device, shown as screw 116. Endplate tray 102 is configured to be attached to pedicle screw support 108 by screws or any other suitable attachment means, such as tray screws 120 shown in FIG. 15.

Figure 19:
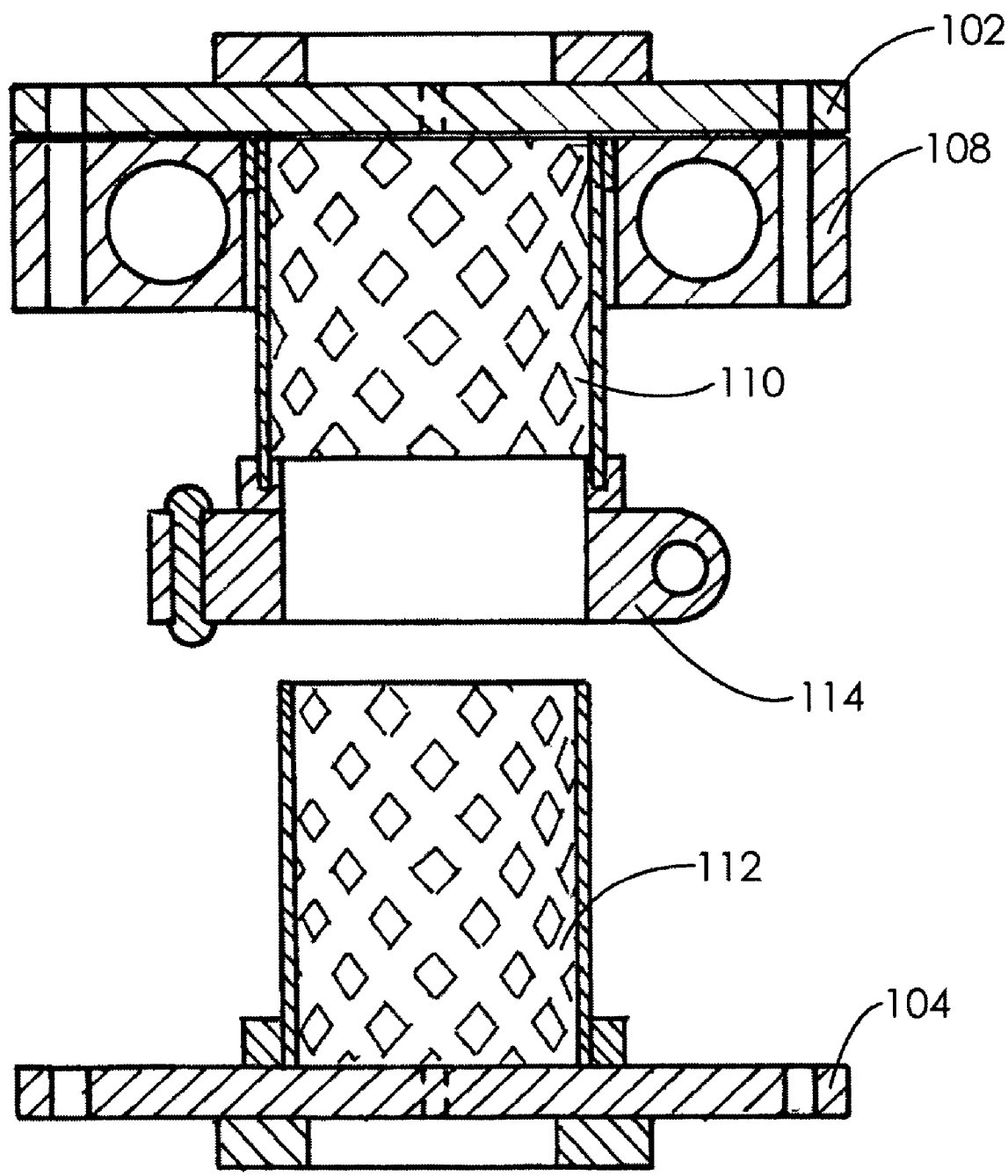
FIG. 19 is a sectional view of the vertebral prosthesis of FIG. 15 prior to assembly.

Referring to FIGS. 17-19, ring 114 is configured to compress shaft upper portion 110 onto shaft lower portion 112 after the proper height adjustment of vertebral prosthesis 100 has been made.

Vertebral prosthesis 100 may be utilized in a similar fashion to vertebral prosthesis 10 in that it is configured to be used with artificial discs of various types by using different endplate trays 102, 104. Further, vertebral prosthesis 100 may be used without artificial discs on one or both ends of the vertebral prosthesis, and may be used as part of a spinal fusion procedure if desired. Referring to FIGS. 15-19, pedicle screw support 108 is configured to receive pedicle screws 118. Preferably, pedicle screw support 108 includes threaded apertures 122 to receive the pedicle screws 118.

Figure 20:
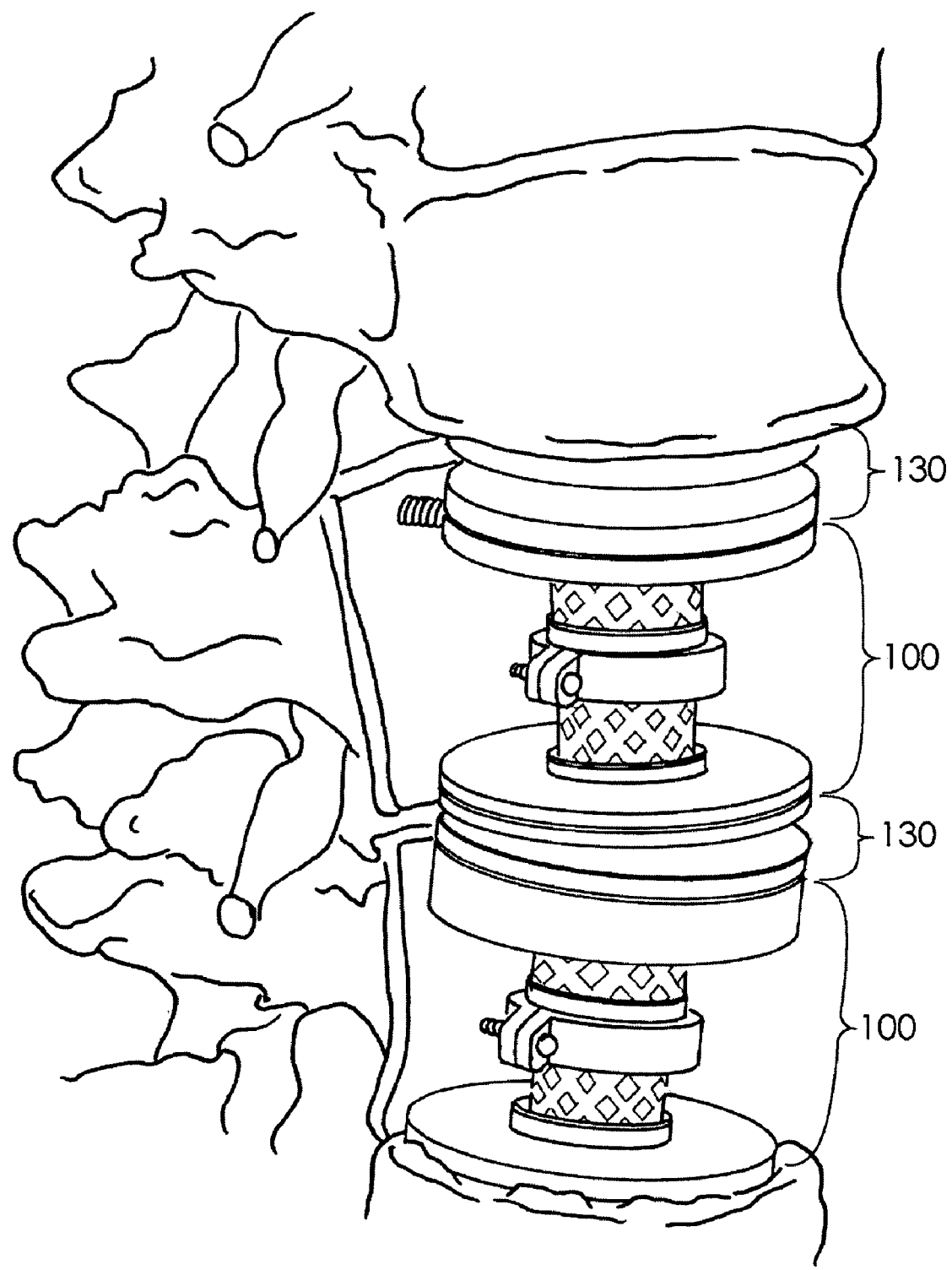
FIG. 20 is a perspective view of two vertebral prostheses and a disc prosthesis inserted into a spine.
Figure 21:
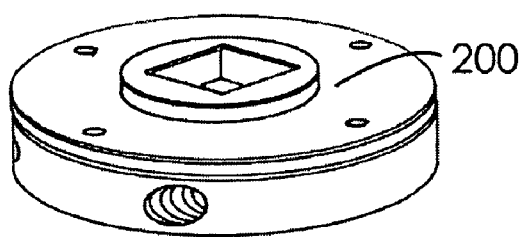
FIGS. 21-24 are perspective views of endplate trays that may be used in conjunction with a vertebral prosthesis.
Figure 22:
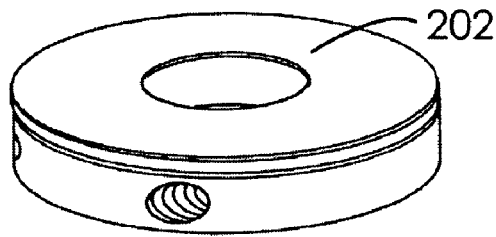
Figure 23:
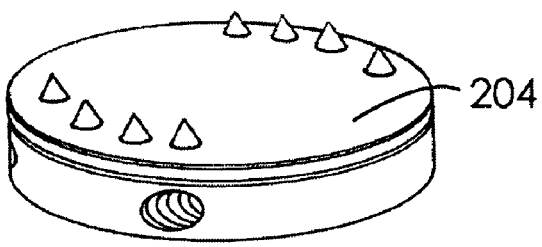
Figure 24:
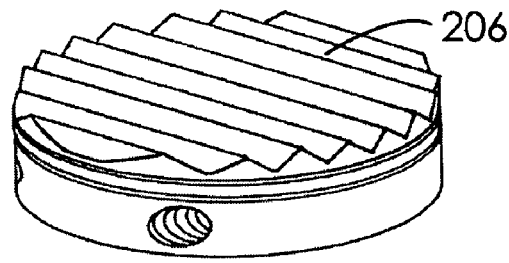

Referring to FIG. 20, two vertebral prostheses may be installed adjacent one another in the case where two adjacent vertebrae require replacement. In such a case, disc prosthesis 130 may be utilized between the upper vertebral prosthesis 100 and the adjacent vertebra and between the two vertebrae prostheses. A disc prosthesis may also be used between the lower vertebral prosthesis and the lower adjacent vertebra. Pedicle screws (not shown) may also be used to further secure one or both of the vertebral prostheses.

Referring to FIGS. 21-24, in order to provide surgical procedure flexibility, the endplate trays of the vertebral prosthesis described herein may have different configurations depending on the type of disc prosthesis that will be used. In an exemplary embodiment, the endplate trays are configured to be threaded or screwed on and off of the shaft of the vertebral prosthesis so that endplate trays may be quickly and easily interchanged depending on the desired configuration. In other embodiments, the endplate trays and shaft may be snapped on or twist-locked onto one another. The surgeon may have the choice of several endplate trays depending on the desired final configuration of the vertebral prosthesis. Four of these endplate tray configurations are shown in FIGS. 21-24 as endplate trays 200, 202, 204, and 206. Of course, other configurations may be utilized within the scope of the present invention.

The vertebral prosthesis described herein may be composed of titanium alloy, although other materials may also be used as suitable. These other materials may be ceramic, composite, or metallic, and may be absorbable or bioactive. Although the shafts are shown as designed with one fitting inside the other, they may also be constructed with two members alongside one another. The mesh version shown in FIGS. 15-20 is useful to promote bone ingrowth. The composition of the endplate trays may be the same as that used for the rest of the vertebral prosthesis but also be other materials such as a high density polyethylene or polyetheretherketone (PEEK) composition.

A vertebra may be replaced or reconstructed using the vertebral prosthesis described herein using the following exemplary procedure. As an initial matter, it must be determined that the vertebra in question must be replaced. The reasons for replacement may include a lumbar burst fracture or a cervical fracture. Prior to operating, a vertebral prosthesis will be chosen on the basis of preoperative sizing. Depending on the location of the vertebra to be replaced or reconstructed, the approach may be lateral or anterior. The natural discs above and below the compromised vertebra may be excised along with the vertebra in question, removing the bone impinging on the nervous structures as well as most of the vertebral body.

The sizing of the vertebral prosthesis will then be confirmed intraoperatively. Where the vertebral prosthesis will be used with replacement disc prostheses on one or both ends, the disc prostheses are attached to the vertebral prosthesis. The superior and inferior vertebrae are then prepared and the vertebral prosthesis in combination with one or both disc prostheses is inserted into place. Where disc prosthetic scaffolds are used, such as those described in co-pending U.S. application Ser. No. 10/619,757, the scaffolds are attached to the adjacent vertebrae prior to insertion of the vertebral prosthesis and attached disc prostheses.

Where the compromised vertebrae is intended to be reconstructed rather than replaced, the endplates of the vertebral body may be preserved along with the adjacent natural spinal discs and the vertebral prosthesis inserted into the vertebra to restore load-bearing function.

If pedicle screws are intended to be used, the anterior or lateral incision is closed and a posterior approach is performed to place the pedicle screws through the pedicles and into a pedicle screw support on the vertebral prosthesis. The posterior incision is then closed.

Preferably, the decision as to whether to use the vertebral prosthesis in combination with artificial disc prostheses is made prior to surgery and the type of disc prostheses decided upon such that the proper endplate tray(s) may be inserted on to the vertebral prosthesis to correspond to the chosen disc prostheses. However, because the vertebral prosthesis is intended to be easily reconfigured to utilize differing endplate trays, changes may be made during the surgical procedure as necessary due to unexpected conditions. As discussed above, endplate trays are differently configured to fit with different types of artificial discs and also may be configured to interface directly with the bone such as by the utilization of posts or teeth to engage the bone.

Based on the preoperative sizing and selections made by the surgeon, the desired endplate trays corresponding to the selected disc prostheses are chosen prior to the surgery. Further, bone graft or a supplement may be placed into the shaft prior to surgery to enhance bone ingrowth as desired. Upon implantation, the vertebral prosthesis is adjusted to have the proper height and is rigidly fixed utilizing the locking ring or other suitable mechanism. After implantation, bone graft or other supplementation may be placed around the device.

While the detailed drawings and specific examples given herein describe various exemplary embodiments, they serve the purpose of illustration only. It is to be understood that the invention is not limited in its application to the details of construction and the arrangements of components set forth in the preceding description or illustrated in the drawings. For example, while a few specific types of disc prostheses that may be used in conjunction with selected endplate trays of the vertebral prosthesis have been shown, other designs of the endplate trays that may be used to cooperate with other disc prostheses are within the scope of the invention. Furthermore, other substitutions, modifications, changes, and omissions may be made in the design, operating conditions, and arrangements of the exemplary embodiments without departing from the scope of the invention as expressed in the appended claims.

What is claimed is:

1. A spinal implant system, comprising:
   a vertebral prosthesis having a support and a prosthesis endplate, the vertebral prosthesis having a longitudinal axis configured to be aligned along the axis of a spine, wherein the support comprises a first portion slidably received in a second portion and wherein the height of the vertebral prosthesis is adjusted by sliding the first portion relative to the second portion, wherein the prosthesis endplate and the support are adapted to be at least one of threaded, snapped, or twist-locked onto one another;
   a locking ring adapted to secure the first portion relative to the second portion;
   an artificial spinal disc, comprising:
      a disc endplate; and
      a disc core coupled to the disc endplate;
      wherein the artificial spinal disc is coupled to the prosthesis endplate, the prosthesis endplate having a structure adapted to interlock with the artificial spinal disc, and further wherein the disc core is configured to allow the disc endplate to move relative to the prosthesis endplate whereby the artificial spinal disc acts as a joint to permit a range of motion between the vertebral prosthesis and the spine; and
   a pedicle screw retainer coupled to at least one of the prosthesis endplate and the support, the pedicle screw retainer comprising:
      a top;
      a bottom;
      a side wall defined between the top and the bottom; and
      at least one aperture defined in the side wall, the aperture having an axis generally perpendicular to the longitudinal axis of the vertebral prosthesis, wherein the aperture is configured to receive a pedicle screw extending through a pedicle located adjacent to the pedicle screw retainer.

2. The spinal implant system of claim 1, wherein the structure prevents rotation of at least a portion of the disc core relative to the prosthesis endplate.

3. The spinal implant system of claim 1, wherein the structure is at least one of a flange and a recess.

4. A spinal implant system, comprising:
   a vertebral prosthesis having a support and a prosthesis endplate, the vertebral prosthesis having a longitudinal axis configured to be aligned along the axis of a spine, wherein the support comprises a first portion slidably received in a second portion and wherein the height of the vertebral prosthesis is adjusted by sliding the first portion relative to the second portion, wherein the prosthesis endplate and the support are adapted to be at least one of threaded, snapped, or twist-locked onto one another;
   a locking ring adapted to secure the first portion relative to the second portion;
   an artificial spinal disc, comprising:
      a disc endplate; and
      a disc core coupled to the disc endplate;
      wherein the artificial spinal disc is coupled to the prosthesis endplate, and further wherein the disc core is configured to allow the disc endplate to move relative to the prosthesis endplate whereby the artificial spinal disc acts as a joint to permit a range of motion between the vertebral prosthesis and the spine; and
   a pedicle screw retainer coupled to at least one of the prosthesis endplate and the support, the pedicle screw retainer comprising:
      a top;
      a bottom;
      a side wall defined between the top and the bottom; and
      at least one aperture defined in the side wall, the aperture having an axis generally perpendicular to the longitudinal axis of the vertebral prosthesis, wherein the aperture is configured to receive a pedicle screw extending through a pedicle located adjacent to the pedicle screw retainer.

5. The spinal implant system of claim 4, further comprising a second prosthesis endplate coupled to the support, the second prosthesis endplate adapted to be coupled to a second artificial spinal disc.

6. The spinal implant system of claim 4, further comprising a second prosthesis endplate coupled to the support, the second prosthesis endplate having teeth adapted to be coupled to a bone.

7. A vertebral prosthesis system including a vertebral prosthesis and a spinal disc prosthesis, the vertebral prosthesis comprising:

a shaft having a longitudinal axis configured to be aligned along the axis of a spine, the shaft comprising a first portion slidably received in a second portion and wherein the height of the vertebral prosthesis is adjusted by sliding the first portion relative to the second portion;

a locking ring adapted to secure the first portion relative to the second portion;

a prosthesis endplate coupled to one end of the shaft, the prosthesis endplate adapted to be implanted adjacent the disc prosthesis, thereby obviating the need to fuse the prosthesis endplate to an adjacent vertebra, wherein the prosthesis endplate and the shaft are adapted to be at least one of threaded, snapped, or twist-locked onto one another; and a pedicle screw retainer coupled to at least one of the shaft and the prosthesis endplate, the pedicle screw retainer comprising:
a top;
a bottom;
a side wall defined between the top and the bottom; and
at least one aperture defined in the side wall, the aperture having an axis generally perpendicular to the longitudinal axis of the shaft, wherein the aperture is configured to receive a pedicle screw extending through a pedicle located adjacent to the pedicle screw retainer;

wherein the disc prosthesis comprises a disc endplate and a disc core coupled to the disc endplate, and further wherein the disc core is configured to allow the disc endplate to move relative to the prosthesis endplate whereby the disc prosthesis acts as a joint to permit a range of motion between the vertebral prosthesis and the spine.

8. The vertebral prosthesis system of claim 7, further comprising a second prosthesis endplate coupled to an other end of the shaft, wherein the second prosthesis endplate comprises one or more teeth configured to directly interface with an other adjacent vertebra, thereby allowing fusion of the vertebral prosthesis with the other adjacent vertebra while preserving motion between the vertebral prosthesis and the adjacent vertebra.

9. The vertebral prosthesis system of claim 7, further comprising a second prosthesis endplate, wherein the second prosthesis endplate is adapted to be implanted adjacent a second disc prosthesis.

10. The vertebral prosthesis system of claim 7, wherein the shaft is at least partially constructed of a mesh.

11. A vertebral prosthesis system comprising:
a vertebral prosthesis comprising:
a shaft having a longitudinal axis configured to be aligned along the axis of a spine;
a first prosthesis endplate coupled to a first end of the shaft, the first prosthesis endplate having a recess, wherein the first prosthesis endplate and the shaft are adapted to be at least one of threaded, snapped, or twist-locked onto one another;
a second prosthesis endplate coupled to a second end of the shaft; and
a pedicle screw retainer coupled to at least one of the shaft, the first prosthesis endplate, and the second prosthesis endplate, the pedicle screw retainer comprising:
a top;
a bottom;
a side wall defined between the top and the bottom; and
at least one aperture defined in the side wall, the aperture having an axis generally perpendicular to the longitudinal axis of the shaft, wherein the aperture is configured to receive a pedicle screw extending through a pedicle located adjacent to the pedicle screw retainer;

an artificial spinal disc, comprising:
a disc endplate; and
a disc core coupled to the disc endplate;
wherein the recess of the first prosthesis endplate is adapted to receive the artificial spinal disc, wherein the recess prevents rotation of at least a portion of the disc core relative to the first prosthesis endplate, and further wherein the disc core is configured to allow the disc endplate to move relative to the first prosthesis endplate whereby the artificial spinal disc acts as a joint to permit a range of motion between the vertebral prosthesis and the spine; and
a pedicle screw received by the at least one aperture of the pedicle screw retainer.

12. The vertebral prosthesis system of claim 11, wherein the second prosthesis endplate comprises one or more teeth configured to interface with an adjacent vertebra.

13. The vertebral prosthesis system of claim 11, wherein the second prosthesis endplate has a second recess adapted to receive a second artificial spinal disc.

14. The vertebral prosthesis system of claim 13, wherein the second recess prevents rotation of at least a portion of a disc core of the second artificial spinal disc relative to the second prosthesis endplate.

15. The vertebral prosthesis system of claim 11, wherein the shaft is adjustable to change the height of the shaft.

16. The vertebral prosthesis system of claim 11, wherein the shaft is at least partially constructed of a mesh.

17. A spinal implant system, comprising:
a vertebral prosthesis having a support and a prosthesis endplate, wherein the support comprises a first portion slidably received in a second portion and wherein the height of the vertebral prosthesis is adjusted by sliding the first portion relative to the second portion, the vertebral prosthesis having a longitudinal axis configured to be aligned along the axis of a spine;
a locking ring adapted to secure the first portion relative to the second portion;
a set of interlocking teeth on the first portion and the second portion, the interlocking teeth adapted to engage one another to secure the first portion relative to the second portion;
a pedicle screw adapted to secure the vertebral prosthesis to a pedicle;
an artificial spinal disc having a disc endplate and a disc core coupled to the disc endplate, wherein the disc core is coupled to the prosthesis endplate, and further wherein the disc core is configured to allow the disc endplate to move relative to the prosthesis endplate whereby the artificial disc acts as a joint to permit a range of motion between the vertebral prosthesis and the spine; and
a pedicle screw retainer coupled to at least one of the prosthesis endplate and the support, the pedicle screw retainer comprising:
a top;
a bottom;
a side wall defined between the top and the bottom; and
at least one aperture defined in the side wall, the aperture having an axis generally perpendicular to the longitudinal axis of the vertebral prosthesis, wherein the aperture is configured to receive a pedicle screw extending through a pedicle located adjacent to the pedicle screw retainer.

18. The spinal implant system of claim 17, further comprising the pedicle screw received by the at least one aperture of the pedicle screw retainer.

19. The spinal implant system of claim 17, wherein the support is at least partially constructed of a mesh.

20. The spinal implant system of claim 17, wherein the prosthesis endplate has a structure adapted to interlock with the artificial spinal disc.

21. The spinal implant system of claim 17, further comprising a second prosthesis endplate coupled to the support, the second prosthesis endplate adapted to be coupled to a second artificial spinal disc.

22. The spinal implant system of claim 17, further comprising a second prosthesis endplate coupled to the support, the second prosthesis endplate having teeth adapted to be coupled to a bone.

* * * * *